US010105123B2

United States Patent
Chen et al.

(10) Patent No.: US 10,105,123 B2
(45) Date of Patent: Oct. 23, 2018

(54) ANALYSIS METHODS OF ULTRASOUND ECHO SIGNALS BASED ON STATISTICS OF SCATTERER DISTRIBUTIONS

(71) Applicant: AmCad BioMed Corporation, Taipei (TW)

(72) Inventors: Argon Chen, Taipei (TW); Yu-Hsin Wang, Taipei (TW); Kuo-Chen Huang, Taipei (TW); Jia-Jiun Chen, Taipei (TW)

(73) Assignee: AMCAD BIOMED CORPORATION, Taipei (TW)

( * ) Notice: Subject to any disclaimer, the term of this patent is extended or adjusted under 35 U.S.C. 154(b) by 335 days.

(21) Appl. No.: 14/962,844

(22) Filed: Dec. 8, 2015

(65) Prior Publication Data

US 2017/0156703 A1 Jun. 8, 2017

(51) Int. Cl.
*A61B 8/08* (2006.01)
*A61B 8/14* (2006.01)
*A61B 8/00* (2006.01)

(52) U.S. Cl.
CPC .......... *A61B 8/5215* (2013.01); *A61B 8/0891* (2013.01); *A61B 8/14* (2013.01); *A61B 8/461* (2013.01)

(58) Field of Classification Search
CPC ......... A61B 8/5215; A61B 8/14; A61B 8/461; A61B 8/0891
See application file for complete search history.

(56) References Cited

U.S. PATENT DOCUMENTS

| 8,092,387 B2 | 1/2012 | Chang et al. |
| 2008/0114242 A1* | 5/2008 | Chang ............... A61B 8/08 600/443 |
| 2011/0306880 A1 | 12/2011 | Li et al. |

FOREIGN PATENT DOCUMENTS

| CN | 102379721 A | 3/2012 |
| TW | 200820946 A | 5/2008 |

OTHER PUBLICATIONS

Tsui et al., "Imaging Local Scatterer Concentrations by the Makagami Statistical Model," Ultrasound in Med. & Biol., vol. 33, No. 4, pp. 608-619, 2007.

* cited by examiner

*Primary Examiner* — Bo J Peng
(74) *Attorney, Agent, or Firm* — Muncy, Geissler, Olds & Lowe, P.C.

(57) ABSTRACT

The invention provides an analysis method of ultrasound echo signals based on statistics of scatterer distributions. The beginning of steps, choosing an ultrasound echo signal as a center, and calculating the signal image values of all ultrasound echo signals within a window block in an ultrasound image data to obtain an ultrasound scatterer value. Then, choosing another ultrasound echo signal as the center to repeat the previous steps until all of ultrasound echo signals may be calculated. The interval between each of ultrasound echo signal is one point distance. Finally, to output an ultrasound scatterer mode image with all ultrasound scatterer values by utilizing color scale. The ultrasound scatterer mode image can assist doctor to confirm the relative region of lesion in a target organ.

3 Claims, 27 Drawing Sheets

| formula 4 | X1 | X2 |
|---|---|---|
| Group 1 | 95 | 5 |
| Group 2 | 95 | 50 |
| Group 3 | 50 | 5 |

FIG.4

| formula 6 | X1 | X2 | X3 | X4 |
|---|---|---|---|---|
| Group 1 | 75 | 5 | 95 | 5 |
| Group 2 | 50 | 5 | 95 | 5 |
| Group 3 | 25 | 5 | 95 | 5 |
| Group 4 | 95 | 5 | 50 | 0 |

Obtaining an ultrasonic image data, wherein the ultrasonic image data comprises a plurality of ultrasound echo signals, each having a signal image value ⟋410

Calculating the signal image values of all ultrasound echo signals in a window block centered at a first ultrasonic echo signal to obtain a first ultrasound scatterer value ⟋420

Calculating the signal image values of all ultrasound echo signals in the window block centered at a second ultrasonic echo signal to obtain a second ultrasound scatterer value ⟋430

Repeatedly calculating the signal image values of all the ultrasound echo signals within the window block with the ultrasound echo signals as centers, to obtain a plurality of ultrasound scatterer values, until the first ultrasound scatterer value to an n-th ultrasound scatterer value being calculated ⟋440

Outputting ultrasound scatterer mode image that display first ultrasound scatterer value to the n-th ultrasound scatterer value by utilizing color scale ⟋450

FIG. 13

ANALYSIS METHODS OF ULTRASOUND ECHO SIGNALS BASED ON STATISTICS OF SCATTERER DISTRIBUTIONS

TECHNICAL FIELD

The present invention relates to a system and a method for analyzing ultrasound echo signals, and in particular, to a system and a method for analyzing ultrasound echo signals based on statistics of scatterer distributions.

BACKGROUND ART

A flow chart 100 of generating an ultrasound grayscale image according to the prior art is shown FIG. 1. Because echo signals received by an ultrasound probe is very weak and complex, it is necessary to display an image through many signal processing steps. In step 110, echo signals data are acquired from an ultrasound probe. However, echo signals still vibrate up and down. In step 120, called a signal demodulation step, negative-phase signals are converted into positive-phase signals, and waveform shape are taken for generating ultrasound envelope data. Because the energy of echo signals is attenuated with the depth of a tissue, the echo signal is required to compensate and amplify through depth gain compensation. Also, because image depth data is indicated by echo duration, the echo signal is necessary to manually adjust for remedy insufficient image contrast by time gain compensation on a common ultrasound machine. Otherwise, the effective dynamic frequency responses for input echo signals are not the same in different electronic devices. A dynamic response range of a current clinical ultrasound system is generally over 100 dB to 140 dB, which indicates that the strongest and the weakest recognizable echo signals differ by a factor of 100,000 to 10,000.000. In step 130, called a data compression step, in order to expand the frequency response range, the ultrasound envelope data is compressed to form grayscale ultrasound data, such as logarithmic compression, wherein an amplification proportion of an echo signal at each location is adjusted (that is, image color scale contrast is adjusted) to highlight weak signals. In step 140, following above processing, a signal processor convert echo time points into depth values according to the sound velocity, and an ultrasound image is displayed with corresponding grayscale values according to the echo signals.

Ultrasound imaging is a very popular technique in medical diagnosis. However, images captured by different ultrasound systems may have different quality in the same lesions. The reason is that grayscale ultrasound data exhibits a granular pattern of white and dark spots, named speckle, so some pathological characteristics with low contrast cannot be characterized. Because an incident wavelength of ultrasound is greater than the diameter of scatterers within the tissue, ultrasound scattering phenomenon occurs. The generated backscattered signals would form speckle. The speckles dim an image of a tiny structure and reduce the contrast and resolution of the ultrasound image. Therefore, a common clinical ultrasound system allows a user to adjust different system parameters, such as the system gain, time-gain compensation (TGC), and dynamic range to filtering or smoothing the speckles influence. Although this is beneficial for clinical anatomical observation, another problem is formed because that physiological or pathological information may be lost. That is why a traditional grayscale image cannot provide the information of characteristics of the tissue.

In order to prevent the influence of the speckles on the image quality, several methods have been successively proposed to reduce the speckles appearance. For example, the Nakagami distribution, originally applied to describe the statistics of radar echoes, is applicable for statistical analysis of ultrasound signals. An ultrasound Nakagami image is a functional ultrasound image for evaluating scatterers arrangement within a tissue.

An ultrasonic imaging technique for differentiating the distribution of scatterers within a tissue is disclosed in US patent U.S. Pat. No. 8,092,387 and Taiwan patent TW1320705, which displays Nakagami parameter m matrix by utilizing pseudo colors, thereby differentiating the distribution of scatterers within the tissue.

A method for dynamically analyzing changes in distribution of scatterers is disclosed in Chinese patent CN102379721, which utilizes a probability density function along with a moving window technique to analyze changes in two-dimensional or three-dimensional scatterer distribution and concentration of ultrasound data, and includes the following steps: calculating a statistical parameter for each of coordinates with a probability density function, wherein the statistical parameter indicates statistical distribution of signal amplitude of speckles of each coordinate within a moving window; and comparing the statistical parameter of each of corresponding coordinates in first ultrasound data and second ultrasound data, to dynamically analyze distribution and concentration variation of scatterers in a sample.

However, applying multiple statistics of scatterer distributions to ultrasound echo signals to evaluate distribution and arrangement of scatterers within a tissue provided in the present invention has not been disclosed in U.S. Pat. No. 8,092,387, TW1320705 and CN102379721. The present invention can assist in providing different clinical information on tissue states, and particularly for distinguishing walls of the blood vessels from internal blood flows. Understanding of the position of the blood vessels can assist a physician in identifying the boundary of an organ or the relative position of the organ with respect to its adjacent organs, which is convenient for providing different clinical information in medical diagnosis.

SUMMARY OF THE INVENTION

The present invention provides a method for analyzing ultrasound echo signals based on statistics of scatterer distributions. The method includes the following steps. First, ultrasound image data is obtained, wherein the ultrasound image data has a plurality of ultrasound echo signals, each having a signal image value.

Then, statistics of the signal image values of all ultrasound echo signals within a window block in the ultrasound image data are performed by choosing a first ultrasound echo signal as a center, and the signal image values are calculated according to a measure of dispersion (MD), a measure of location (ML) or any combination thereof, to obtain a first ultrasound scatterer value; and further, statistics of the signal image values of all ultrasound echo signals within the window block in the ultrasound image data are performed with a second ultrasound echo signal as a center, to obtain a second ultrasound scatterer value, wherein the second ultrasound echo signal is separated from the first ultrasound echo signal by at least one point distance.

Using the same point distance as intervals, the signal image values of all the ultrasound echo signals within the window block are repeatedly calculated by choosing the respective ultrasound echo signals as centers, to obtain a plurality of ultrasound scatterer values, until the first ultrasound scatterer value to an n-th ultrasound scatterer value being calculated.

Finally, an ultrasound scatterer mode image is formed that displays the first ultrasound scatterer value to the n-th ultrasound scatterer value by utilizing color scale.

The present invention further provides a system for analyzing ultrasound echo signals based on statistics of scatterer distributions.

The system is based on the above method and performs statistical analysis of signal image values of ultrasound image data through multiple statistics of scatterer distributions, so as to evaluate distribution and arrangement of scatterers within a tissue, thereby assisting in providing clinical information on tissue state. The system comprises a capturing device, an analyzing unit, and a display unit.

The capturing device is used for obtaining ultrasound image data, wherein the ultrasound image data has a plurality of ultrasound echo signals, each having a signal image value.

The analyzing unit is connected to the capturing device for analyzing the ultrasound echo signals, wherein the analyzing processes includes: choosing a first ultrasound echo signal as a center, calculating the signal image values of all ultrasound echo signals within a window block in the ultrasound image data according to a measure of MD, an ML or any combination thereof, to obtain a first ultrasound scatterer value; then, choosing a second ultrasound echo signal as a center, calculating the signal image values of all ultrasound echo signals within the window block in the ultrasound image data, to obtain a second ultrasound scatterer value, wherein the second ultrasound echo signal is separated from the first ultrasound echo signal by at least one point distance; and at the same intervals of the point distance, repeatedly performing statistical analysis of the signal image values of all the ultrasound echo signals within the window blocks by choosing respective ultrasound echo signals as centers, to obtain a plurality of ultrasound scatterer values, until the first ultrasound scatterer value to an n-th ultrasound scatterer value being calculated.

The display unit is connected to the analyzing unit for outputting an ultrasound scatterer mode image that displays the first ultrasound scatterer value to the n-th ultrasound scatterer value by utilizing color scale.

BRIEF DESCRIPTION OF DRAWINGS

FIG. 4 shows a table containing three groups different statistical range values according to a formula 4 of the present invention;

FIG. 8 shows a table containing four groups different statistical range values according to a formula 6 of the present invention;

FIG. 13 is a flow chart of a method for analyzing ultrasound echo signals based on statistics of scatterer distributions according to an embodiment of the present invention.

DETAILED DESCRIPTION OF THE PREFERRED EMBODIMENTS

In order to fully understand the effects of the present invention, preferred embodiments are described below in combination with the accompanying drawings.

The present invention provides a method and a system for analyzing ultrasound echo signals based on statistics of scatterer distributions, wherein analysis of signal image values of ultrasound image data are performed based on statistics of scatterer distributions, so as to evaluate distribution and arrangement of scatterers within a tissue, thereby assisting in tissue characterization and providing clinical information on tissue state.

Figure 1:
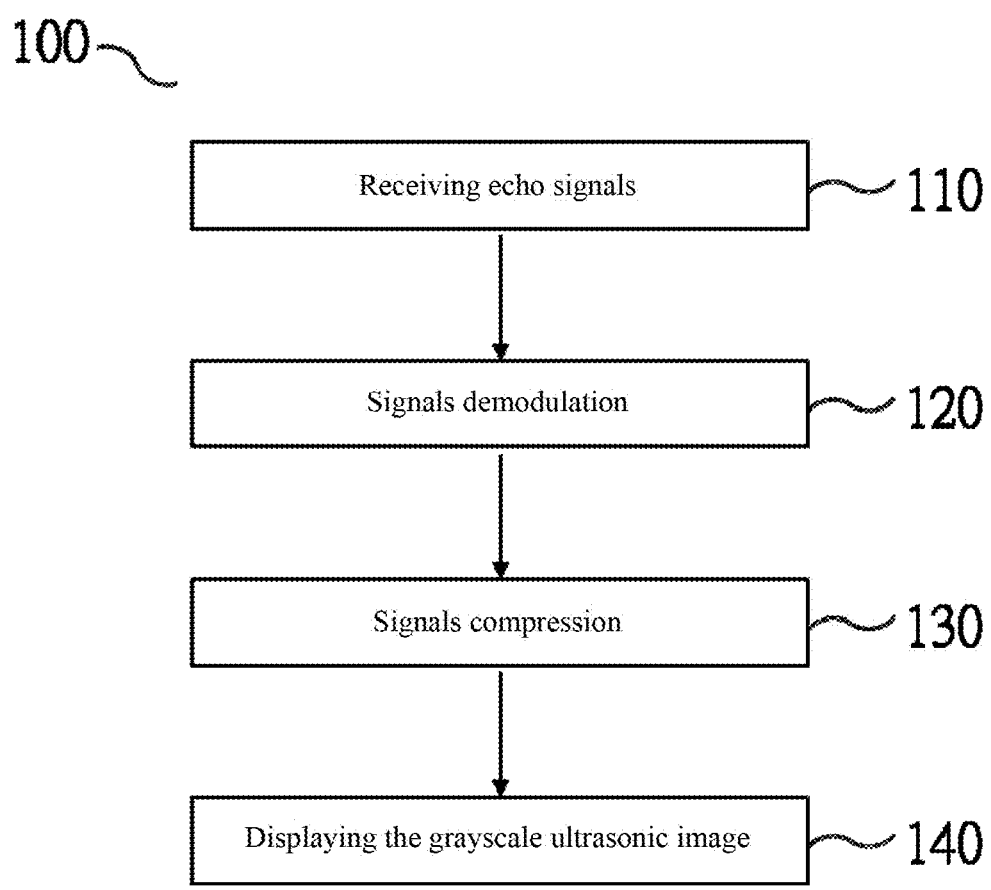
FIG. 1 is a flow chart of generating a grayscale ultrasound image according to a prior art.
Figure 2:
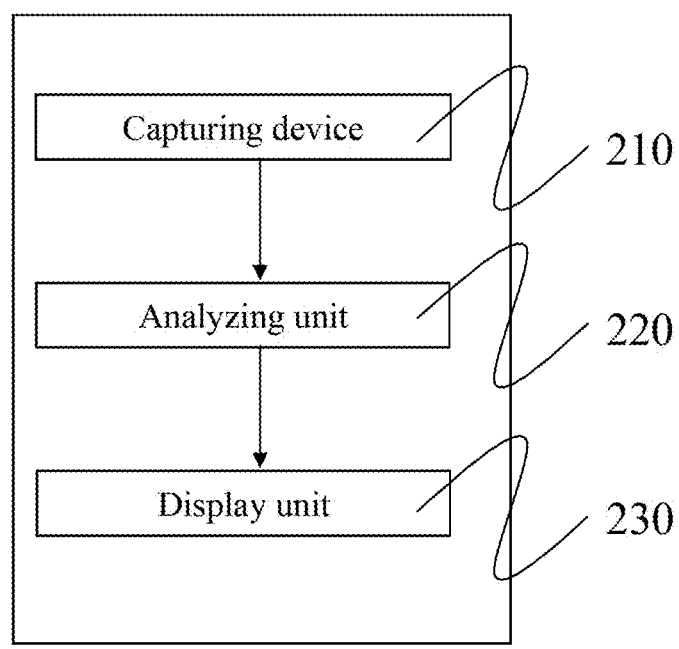
FIG. 2 is a schematic diagram of a system designed for a method for analyzing ultrasound echo signals based on statistics of scatterer distributions according to the present invention.
Figure 3:
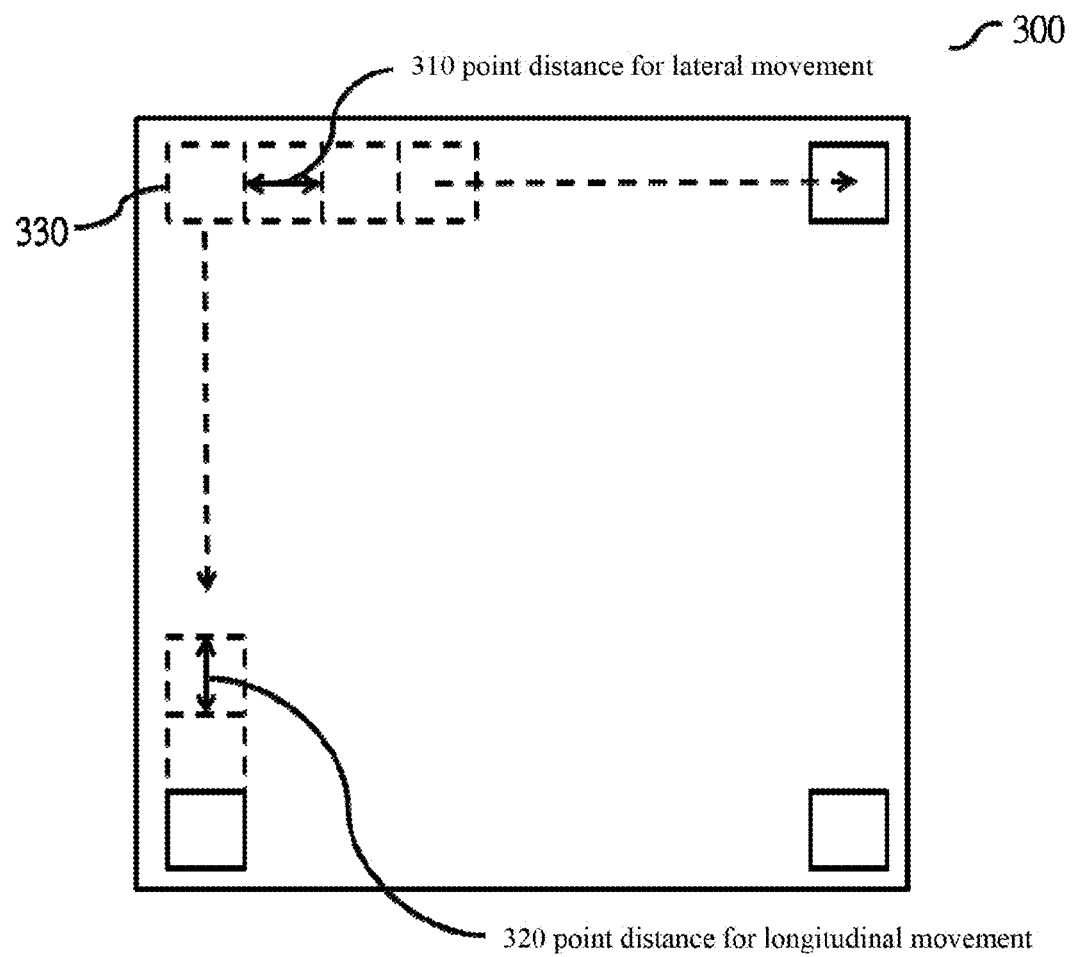
FIG. 3 is a schematic view for illustrating operation of moving a window block in an ultrasound image according to the present invention.

A schematic diagram of a system designed for analyzing ultrasound echo signals based on statistics of scatterer distributions is shown in FIG. 2. An ultrasound image system 200 of the present invention comprises a capturing device 210, an analyzing unit 220, and a display unit 230. A schematic view for illustrating operation of a moving window block 330 in an ultrasound image according to the present invention is shown in FIG. 3.

The ultrasound image system 200 captures an image of a tissue through the capturing device 210 (for example, an ultrasound probe) to obtain ultrasound image data 300, wherein the ultrasound image data 300 includes a plurality of ultrasound echo signals, each having a signal image value.

Then, the analyzing unit 220 is connected to the capturing device 210 for analyzing the ultrasound image data 300. For this end, a user needs to set a window block 330 in the ultrasound image data 300, wherein the size of the window block 330 is set to be N times the pulse length of transducer, with N being a nonzero natural number. Then, with an upper-left corner of the ultrasound image data 300 as a starting position, statistical analysis of the signal image values of all ultrasound echo signals within the window block 330 are performed, and the signal image values are calculated according to a measure of dispersion (MD), a measure of location (ML) or any combination thereof, to obtain a ultrasound scatterer value.

The analyzing unit 220 of the present invention performs the following operation on the ultrasound image data 300: choosing a first ultrasound echo signal as a center, calculating the signal image values of all ultrasound echo signals within a window block 330 in the ultrasound image data, to obtain a first ultrasound scatterer value.

Then, the analyzing unit 220 moves the window block 330 at a fixed or a non-fixed intervals The non-fixed interval illustrates the window block 330 moves with different point distances in longitudinal and lateral directions, for example, six point distances of lateral movement 310 and thirty-six point distances of longitudinal movement 320. When the window block is moved laterally and longitudinally for the corresponding point distances, a new ultrasound scatterer value is calculated by the analyzing unit 220.

For example, after the first ultrasound scatterer value is taken by the analyzing unit 220, the window block 330 is moved laterally for a six point distances and longitudinally for a thirty-six point distances from the first ultrasound echo signal, and a second ultrasound echo signal is selected. Choosing the second ultrasound echo signal as a center, the analyzing unit 220 calculates the signal image values of all ultrasound echo signal within the window block 330 in the ultrasound image data, to obtain a second ultrasound scatterer value.

The window block 330 is repeatedly moved at intervals of the point distance, and a plurality of ultrasound scatterer values is calculated by the analyzing unit 220 until the first ultrasound scatterer value to an n-th ultrasound scatterer value being calculated. When a point distance between the ultrasound echo signals is greater than one point distance, an interpolating function is used to obtain complete ultrasound scatterer values.

ML generally refers to a measure of location in a data set, including a mode value, a statistical percentile value, or a mean value. In an embodiment, the analyzing unit 220 calculates the signal image values of ultrasound echo signals within the window block 330 with the respective ultrasound echo signals as centers to obtain a plurality of ultrasound scatterer values (S), a first mode value to an n-th mode value, by the following formula 1:

$$S = \text{Mode (window block)} \quad \text{[formula 1]}$$

In another embodiment, the analyzing unit 220 calculates the signal image values of ultrasound echo signals within the window block 330 with the respective ultrasound echo signals as centers, to obtain a plurality of ultrasound scatterer values (S), a first X-th percentile value to an n-th X-th percentile value, by the following formula 2, wherein the statistical percentile may be set by a user. When X-th is 50, the statistical percentile is equal to a median value.

$$S = \text{Percentile } X\text{-th (window block)} \quad \text{[formula 2]}$$

In another embodiment, the analyzing unit 220 calculates the signal image values of ultrasound echo signals within the window block 330 with the respective ultrasound echo signals as centers, to obtain a plurality of ultrasound scatterer values (S), a first mean value to an n-th mean value, by the following formula 3.

$$S = \text{Mean (window block)} \quad \text{[formula 3]}$$

MD generally refers to a measure of dispersion of data set, including a standard deviation value or a statistical range value. In an embodiment, the analyzing unit 220 calculates the signal image values of all ultrasound echo signals within the window block 330 with the respective ultrasound echo signals as centers, to obtain a plurality of ultrasound scatterer value (S), a first statistical range value to an n-th statistical range value, by the following formula 4, wherein the statistical range value is calculated by subtracting a second statistical percentile (Percentile X2) value from a first statistical percentile (Percentile X1) value, wherein the statistical percentiles may be set by the user $$S = (\text{Percentile } X1(\text{window block}) - \text{Percentile } X2(\text{window block}) \quad \text{[formula 4]}$$

A table containing three groups different statistical range values according to the formula 4 of the present invention is shown FIG. 4, wherein two different percentile values are represented by variables X1 and X2 in this table. FIG. 5A to FIG. 5E show ultrasound scatterer mode images generated according to the formula 4 using first group setting (X1=95 and X2=5) listed on FIG. 4 and the corresponding traditional grayscale image from normal liver tissue to severe liver fibrosis cases. The results show that different distribution and arrangement of scatterers within liver tissue are clearly evaluated.

FIG. 6A to FIG. 6E show ultrasound scatterer mode images generated according to the formula 4 using second group setting (X1=95 and X2=50) listed on FIG. 4 and the corresponding traditional grayscale image from normal liver tissue to severe liver fibrosis cases. The results show that different distribution and arrangement of scatterers within liver tissue are clearly evaluated. FIG. 7A to FIG. 7E show ultrasound scatterer mode images generated according to the formula 4 using third group setting (X1=50 and X2=5) listed on FIG. 4 and the corresponding traditional grayscale image from normal liver tissue to severe liver fibrosis cases. The results show that different distribution and arrangement of scatterers within liver tissue are clearly evaluated In another embodiment, the analyzing unit 220 calculates the signal image values of all ultrasound echo signals within the window block 330 with the respective ultrasound echo signals as centers, to obtain a plurality of ultrasound scatterer values (S), a first standard deviation value to an n-th standard deviation value, by the following formula 5.

$$S = STD \text{ (window block)} \quad \text{[formula 5]}$$

Further, in the present invention, an ultrasound scatterer value is obtained by with any combination of MDs and MLs of the signal image values.

For example, an ultrasound scatterer value is obtained by dividing a first MD of the signal image values by a second MD of the signal image values and raising to a power constant (m), and multiplying by a weighting constant (C), represented by $S = C^*(MD1/MD2)^m$. In an embodiment, when C is 1, m is 1, first MD and second MD are statistical range values, the analyzing unit 220 divides a first statistical range value, the difference value between X1 and X2, of the signal image values by a second statistical range value, the difference value between X3 and X4, of the signal image values to obtain a plurality of ultrasound scatterer values (S) by the following formula 6.

$$S = (\text{Percentile } X1 \text{ (window block)} - \text{Percentile } X2 \text{ (window block)})/(\text{Percentile } X3 \text{ (window block)} - \text{Percentile } X4 \text{ (window block)}) \quad \text{[formula 6]}$$

Figure 9A:
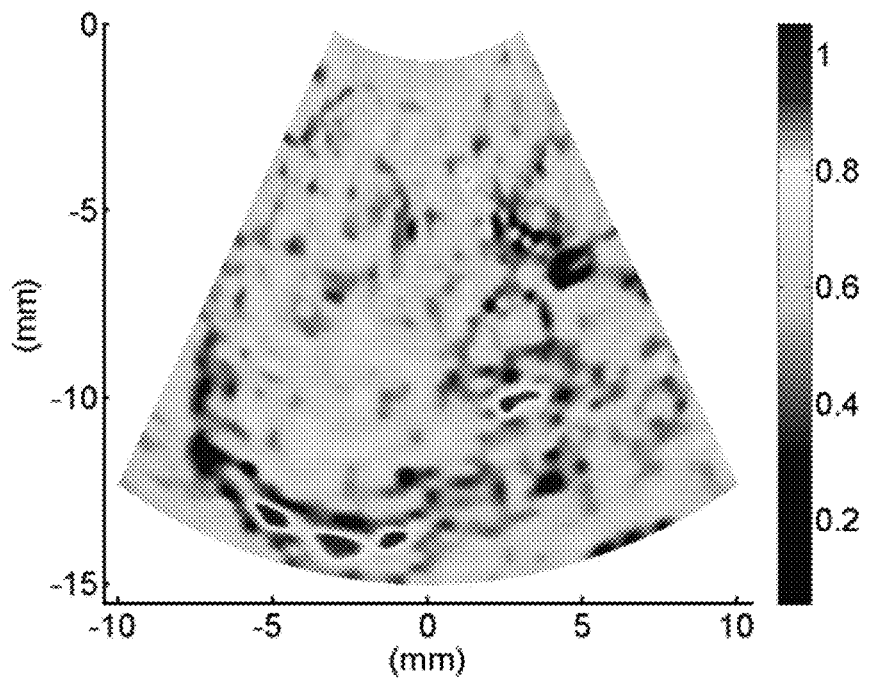
FIG. 9A to FIG. 9D show ultrasound scatterer mode images generated according to the formula 6 using first to fourth groups setting listed on FIG. 8, respectively.
Figure 9B:
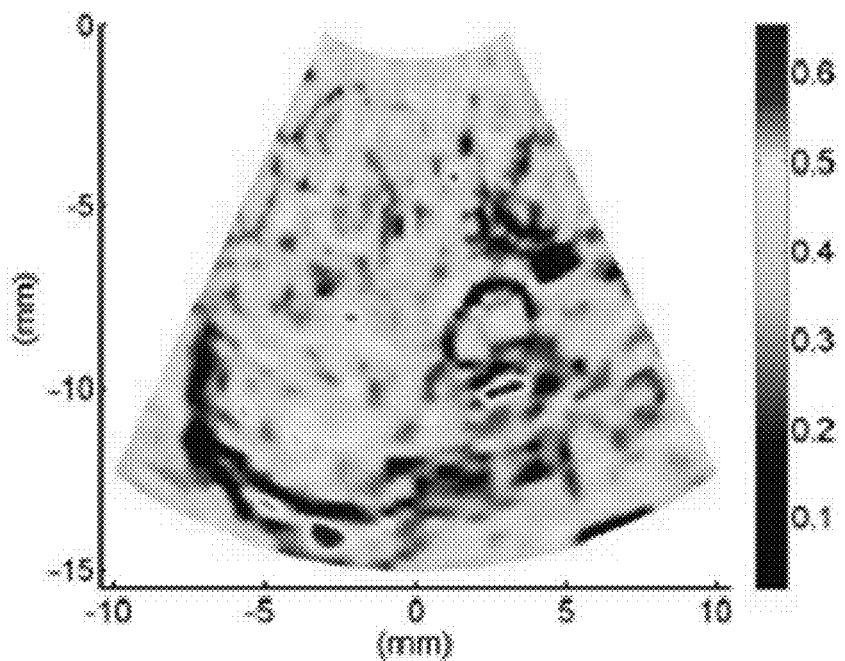
Figure 9C:
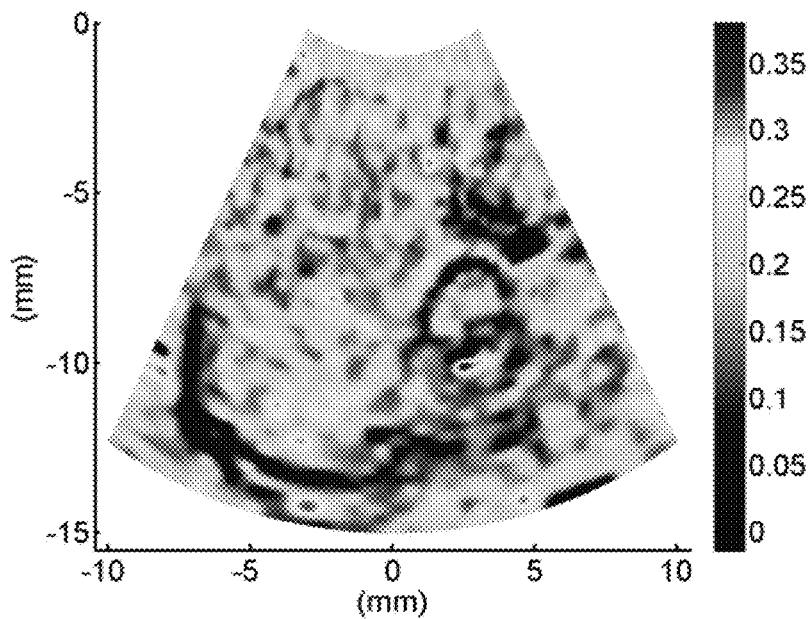
Figure 9D:
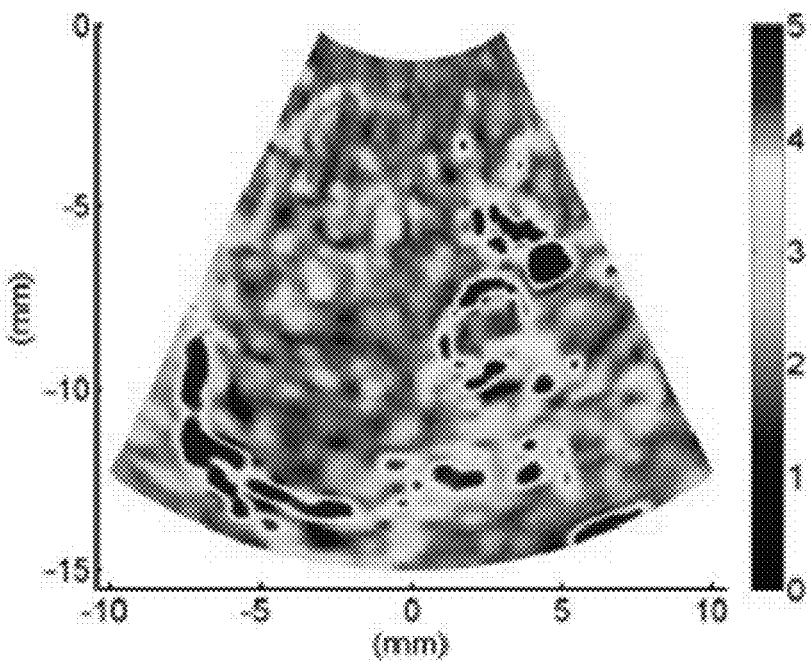
Figure 9E:
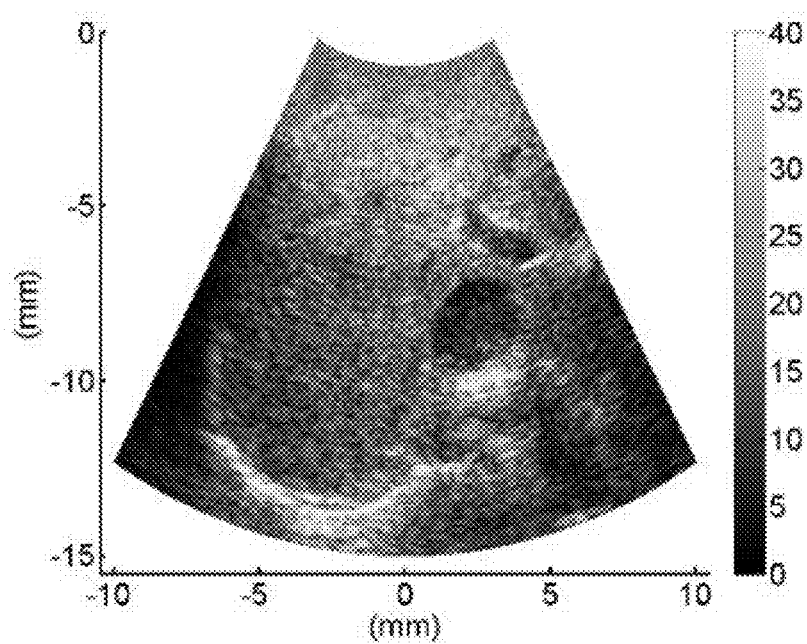
FIG. 9E is an corresponding traditional grayscale ultrasound image.

A table containing four groups different statistical range values according to the formula 6 of the present invention is shown in FIG. 8, wherein four different percentile values are represented by variables X1, X2, X3 and X4. FIG. 9A to FIG. 9D show ultrasound scatterer mode images generated according to the formula 6 with the different groups setting in the table of FIG. 8. FIG. 9E is a traditional grayscale ultrasound image data. An ultrasound scatterer mode image generated according the formula 6 with variables of first group setting (X1=75, X2=5, X3=95, and X4=5) as statistics is shown in FIG. 9A. An ultrasound scatterer mode image generated according the formula 6 with variables of second group setting (X1=50, X2=5, X3=95, and X4=5) as statistics is shown in FIG. 9B. An ultrasound scatterer mode image generated according the formula 6 with variables of third group setting (X1=25, X2=5, X3=95, and X4=5) as statistics is shown in FIG. 9C. An ultrasound scatterer mode image generated according the formula 6 with variables of fourth group setting (X1=95, X2=5, X3=50, and X4=0) as statistics is shown in FIG. 9D. The results show that the user can characterize the distribution and arrangement of scatterers within liver tissue. Moreover, the inferior cava vena (ICV) and portal vein are also can be clearly recognized.

In another embodiment, when C is 1, m is 1, first MD is statistical range value, and second MD is standard deviation value, the analyzing unit 220 divides a statistical range value, the difference value between X1 and X2, of the signal image values by a standard deviation value of the signal image values to obtain a plurality of ultrasound scatterer values (S) by the following formula 7.

$$S=(\text{Percentile } X1 \text{ (window block)} - \text{Percentile } X2 \text{ (window block)})/STD \text{ (window block)} \quad \text{[formula 7]}$$

For another example, a ultrasound scatterer value is obtained by dividing a difference value between of a first ML and a second ML of the signal image values by the MD of the signal image values and raising to a power constant (m), and multiplying by a weighting constant (C), represented by $S=C*((ML1-ML2)/MD)^m$. In an embodiment, when C is 1, m is 1, first ML is mode value, second ML is mean value, and MD is a statistical range value, the analyzing unit 220 subtracts a mean value of the signal image values from a mode value of the signal image values to obtain a difference value, then divides the difference value by a statistical range value of the signal image values to obtain ultrasound scatterer values (S), represented by the following formula 8.

$$S=(\text{Mode (window block)} - \text{Mean (window block)})/(\text{Percentile } X1 \text{ (window block)} - \text{Percentile } X2 \text{ (window block)}) \quad \text{[formula 8]}$$

The display unit 230 can display an ultrasound scatterer mode image generated according to the formula 8 of the present invention as shown in FIG. 9. The result shows that the user can characterize the distribution and arrangement of scatterers within liver tissue. Moreover, the inferior cava vena (ICV) and portal vein are also can be clearly recognized.

In another embodiment, when C is 1, m is 1, first ML is mode value, second ML is mean value, and MD is standard deviation value, the analyzing unit 220 subtracts a mean value of the signal image values from a mode value of the signal image values to obtain a difference value, then divides the difference value by a standard deviation value of the signal image values to obtain ultrasound scatterer values (S), represented by the following formula 9:

$$S=(\text{Mode (window block)} - \text{Mean (window block)})/STD \text{ (window block)} \quad \text{[formula 9]}$$

Figure 10:
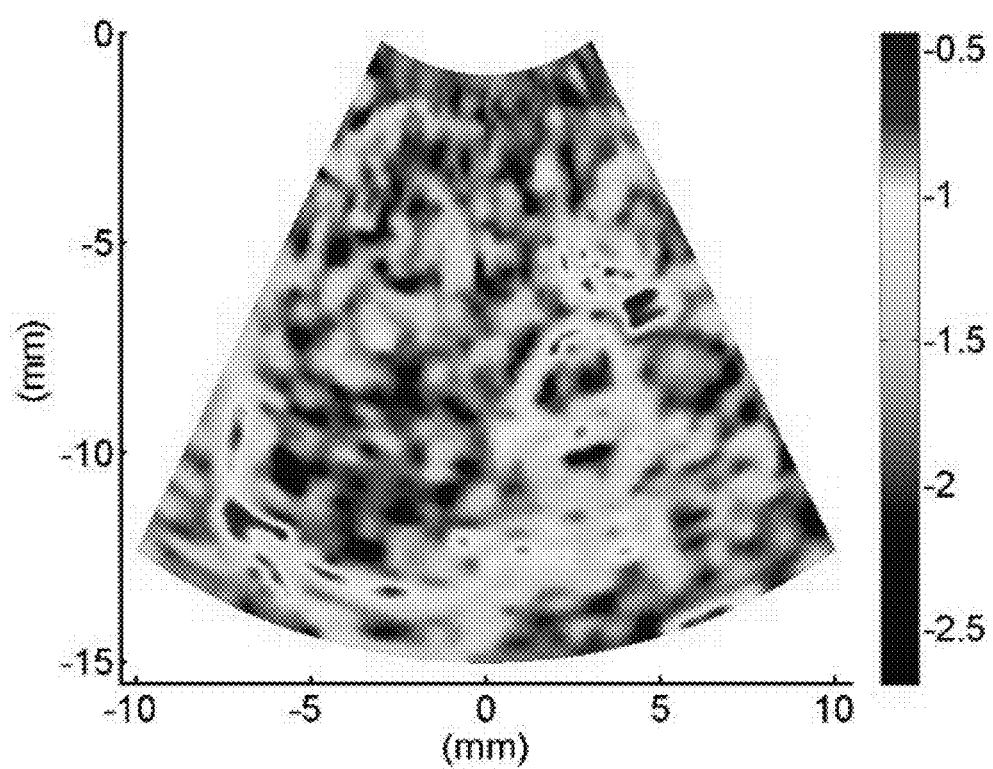
FIG. 10 is an ultrasound scatterer mode image generated according to a formula 9 of the present invention.

The display unit 230 can display an ultrasound scatterer mode image generated according to the formula 9 of the present invention as shown in FIG. 10. The result shows that the user can characterize the distribution and arrangement of scatterers within liver tissue. Moreover, the inferior cava vena (ICV) and portal vein are also can be clearly recognized.

In another embodiment, when C is 1, m is 1, first ML is median value, second ML is mean value, and MD is standard deviation value, the analyzing unit 220 subtracts a mean value of the signal image values from a median value of the signal image values to obtain a difference value, then divides the difference value by a standard deviation value of the signal image values to obtain ultrasound scatterer values (S), represented by the following formula 10.

$$S=(\text{Median (window block)} - \text{Mean (window block)})/STD \text{ (window block)} \quad \text{[formula 10]}$$

Figure 11:
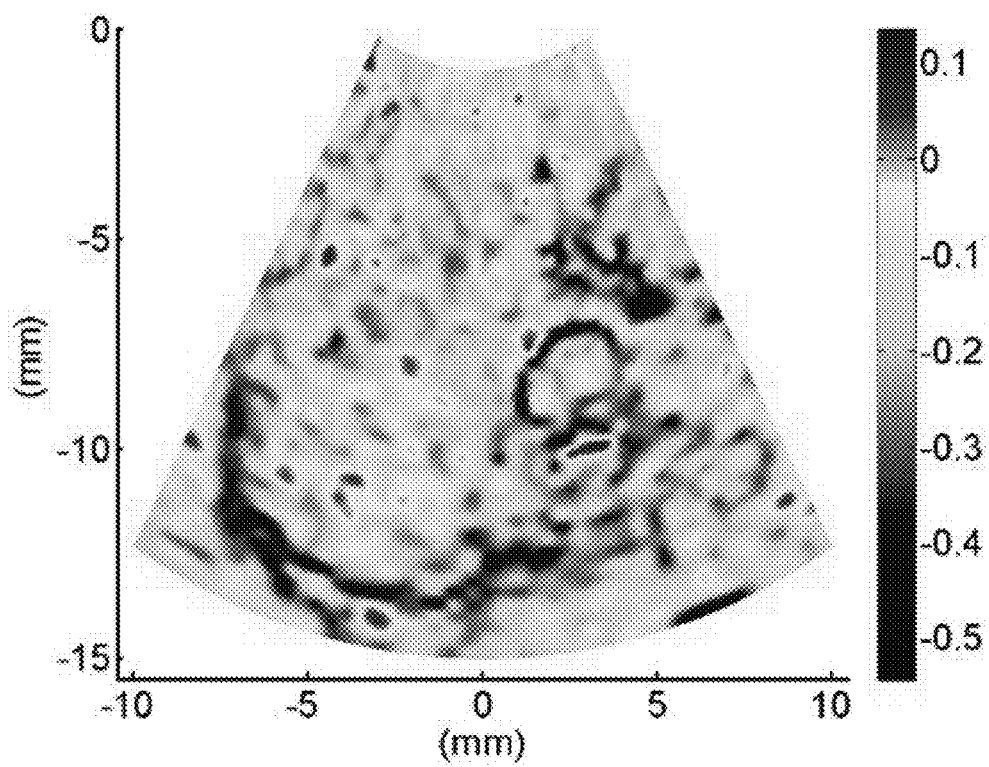
FIG. 11 is an ultrasound scatterer mode image generated according to a formula 10 of the present invention.

The display unit 230 can display an ultrasound scatterer mode image generated according to the formula 10 of the present invention as shown in FIG. 11. The result shows that the user can characterize the distribution and arrangement of scatterers within liver tissue. Moreover, the inferior cava vena (ICV) and portal vein are also can be clearly recognized.

For another example, ultrasound scatterer values are obtained by dividing the MD of the signal image values by the ML of the signal image values and raising to a power constant(m), and multiplying by a weighting constant (C), represented by $S=C*(MD/ML)^m$. In an embodiment, when C is 1, m is 1, MD is standard deviation value, and ML is mean value, the analyzing unit 220 divides a standard deviation value of the signal image values by a mean value of the signal image values to obtain ultrasound scatterer values (S), represented by the following formula 11:

$$S=STD \text{ (window block)}/\text{Mean (window block)} \quad \text{[formula 11]}$$

Figure 12:
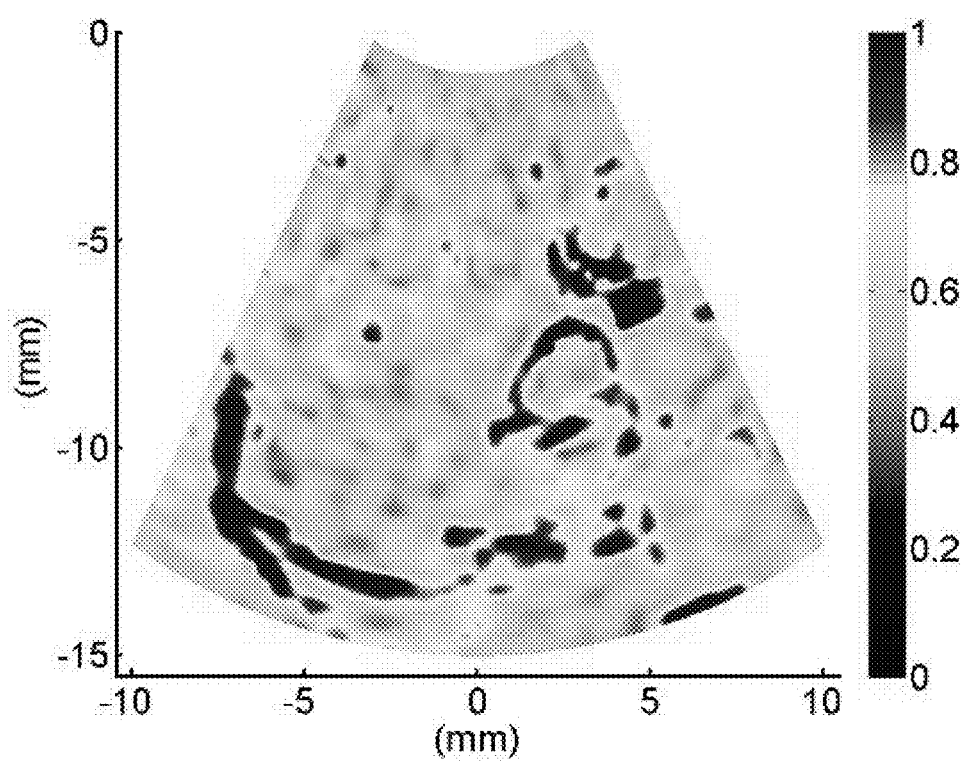
FIG. 12 is an ultrasound scatterer mode image generated according to a formula 11 of the present invention.

The display unit 230 can display an ultrasound scatterer mode image generated according to the formula 11 of the present invention as shown in FIG. 12. The result shows that the user can characterize the distribution and arrangement of scatterers within liver tissue. Moreover, the inferior cava vena (ICV) and portal vein are also can be clearly recognized.

In the present invention, the user can easily assess the distribution of the ultrasound scatterers by generating ultrasound scatterer mode image based on statistic methods. It can distinguish the blood vessels from normal tissue and identify the walls of the blood vessels (e.g. inferior cava vena (ICV) and portal vein). Further, understanding position of the blood vessels can assist a physician in identifying the boundary of an observed organ or the relative location of the observed organ with respect to its adjacent organs can be determined, thereby providing different clinical information (FIG. 8 to FIG. 12).

Figure 5A:
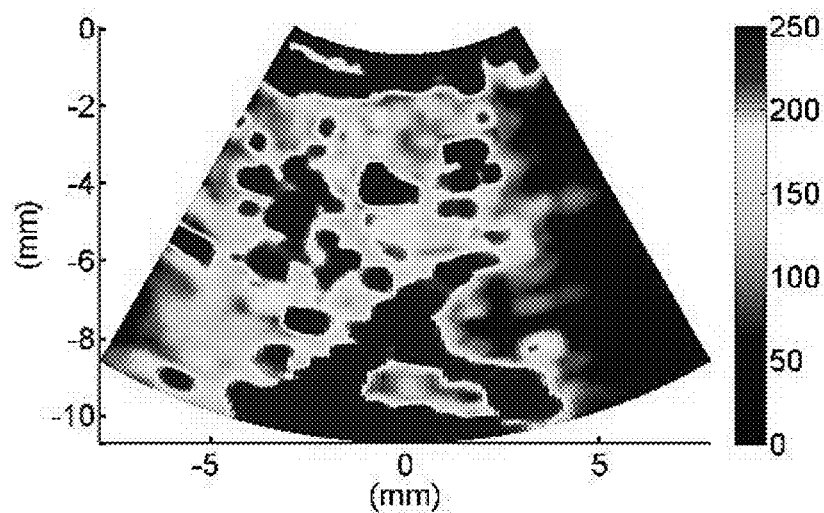
FIG. 5A to FIG. 5E show ultrasound scatterer mode images generated according to the formula 4 using first group setting listed on FIG. 4, and corresponding traditional grayscale ultrasound images.
Figure 5A:
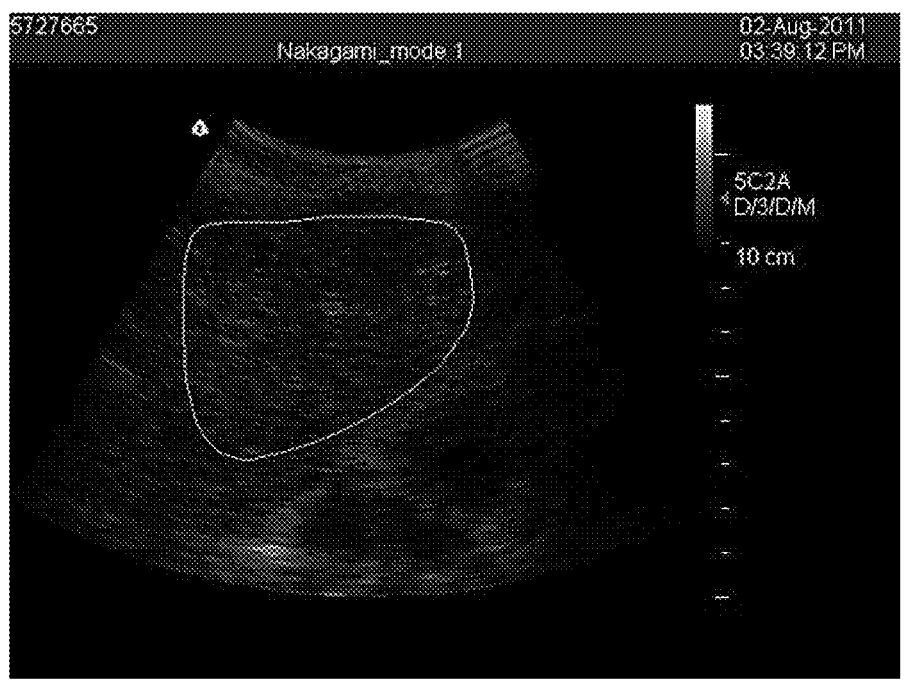
Figure 5B:
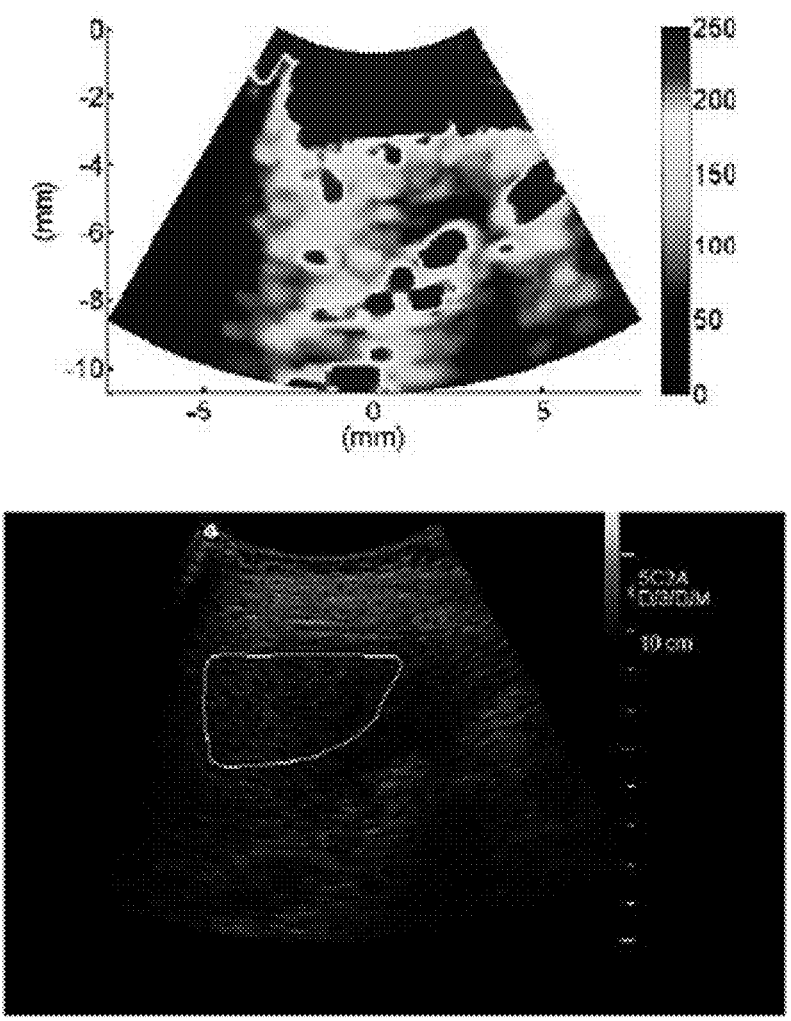
Figure 5C:
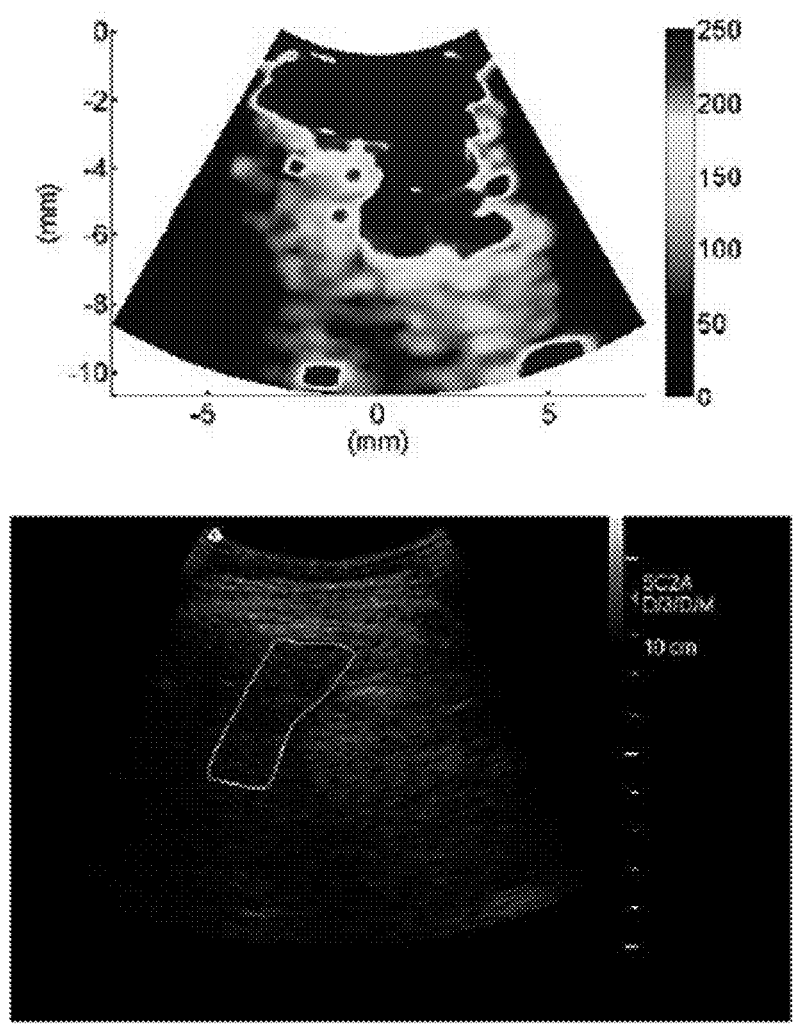
Figure 5D:
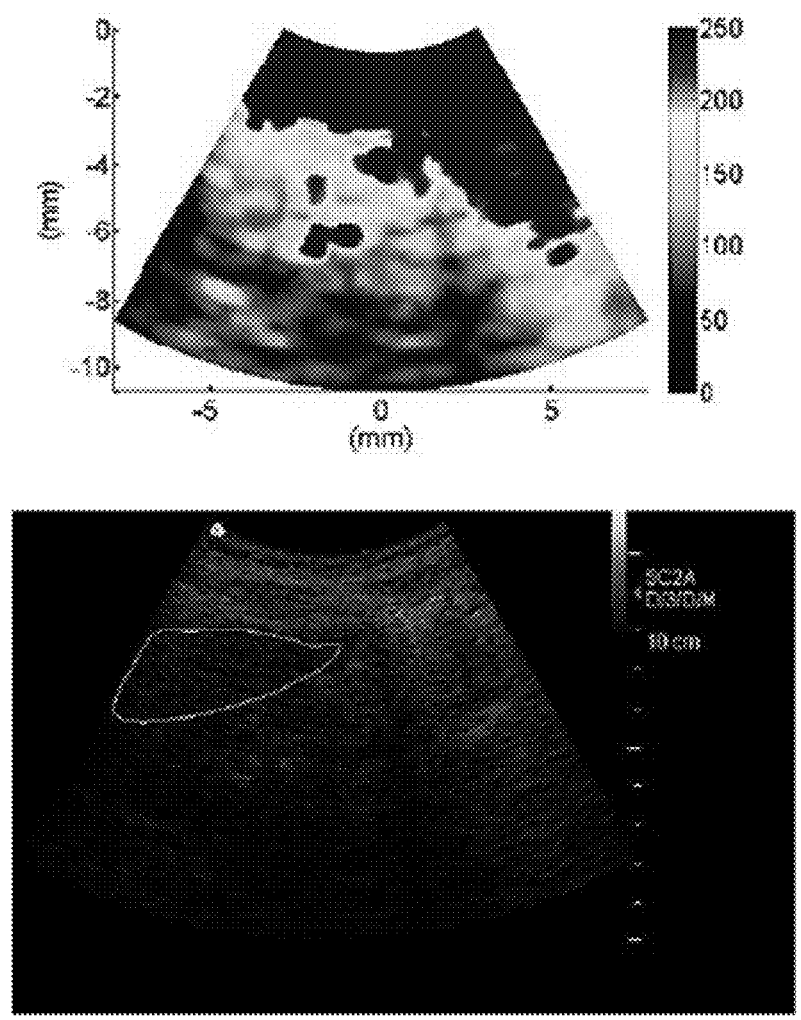
Figure 5E:
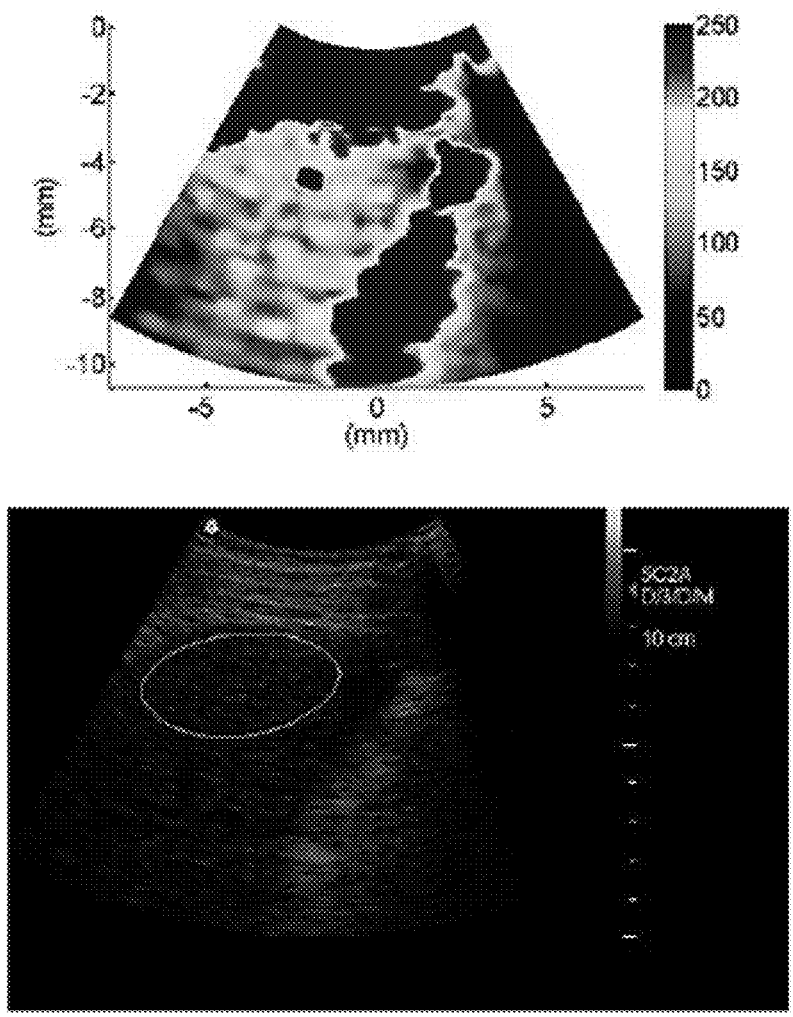
Figure 6A:
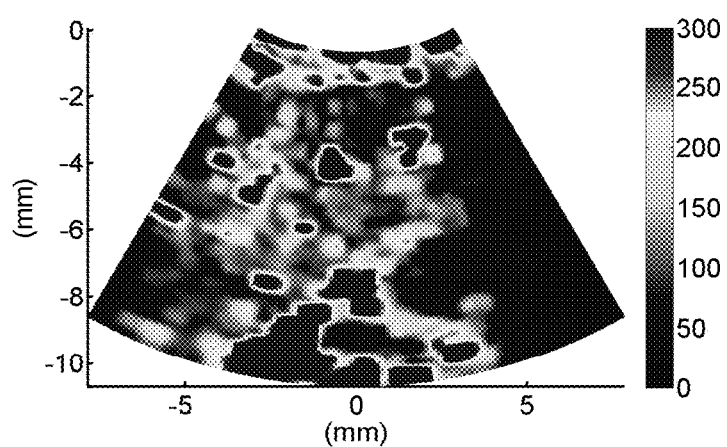
FIG. 6A to FIG. 6E show ultrasound scatterer mode images generated according to the formula 4 using second group setting listed on FIG. 4, and corresponding traditional grayscale ultrasound images.
Figure 6A:
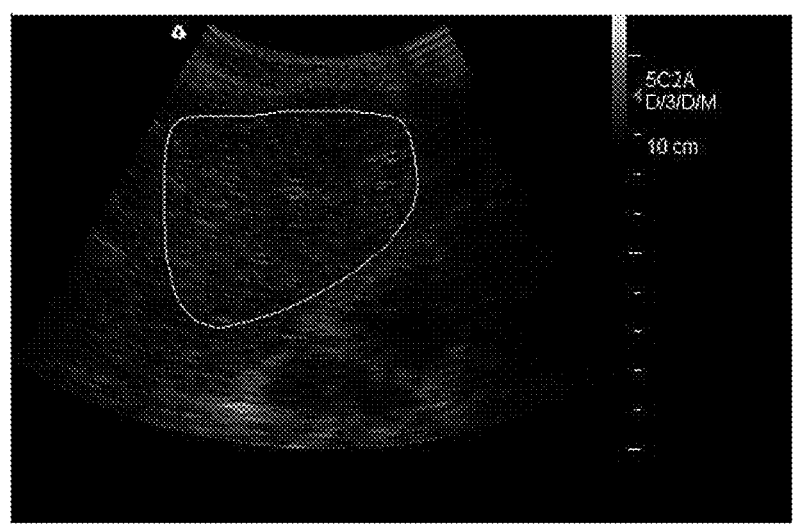
Figure 6B:
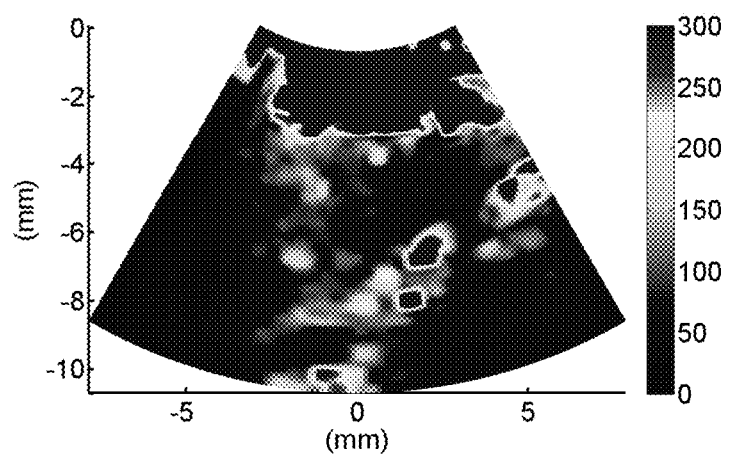
Figure 6B:
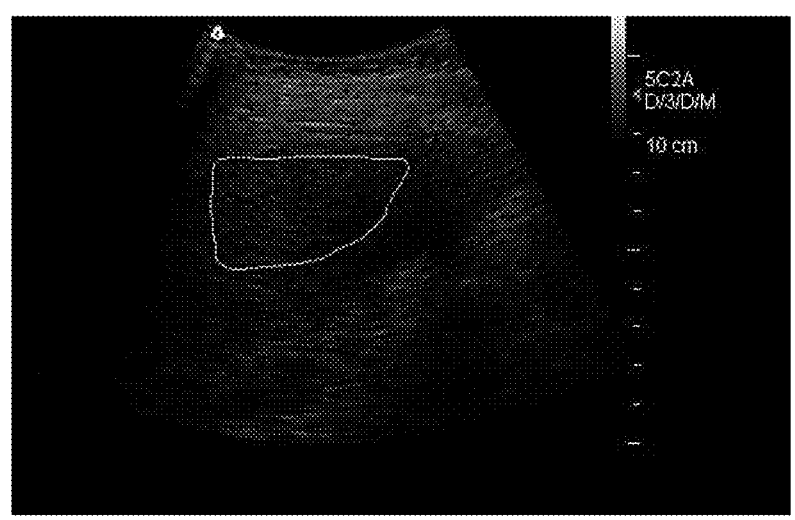
Figure 6C:
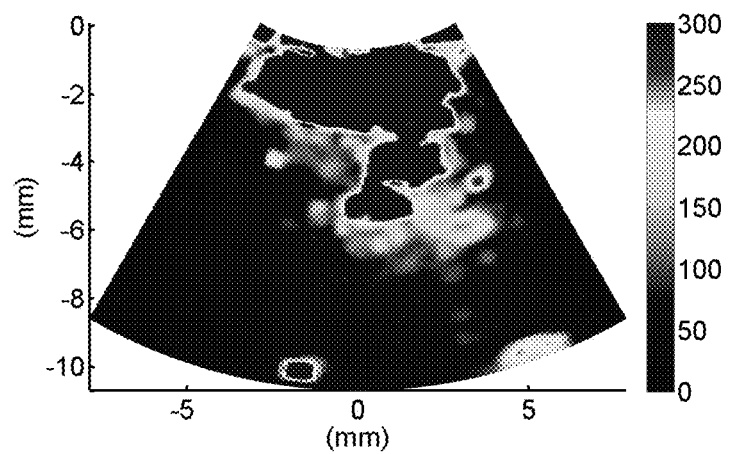
Figure 6C:
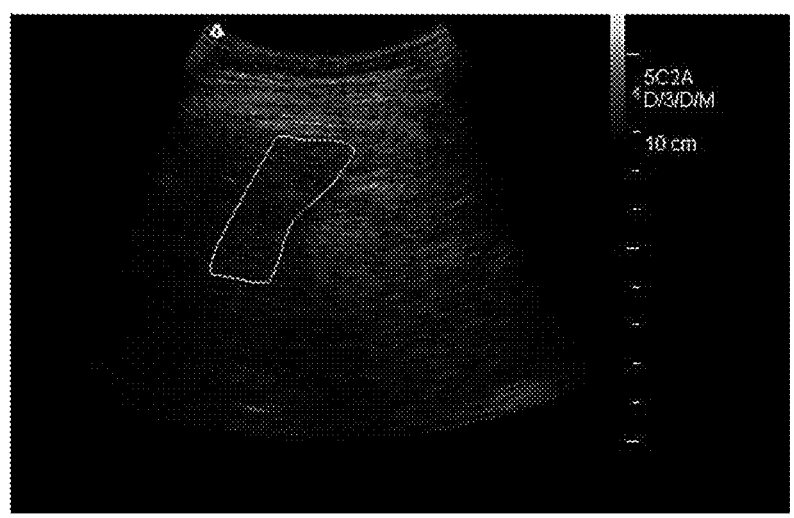
Figure 6D:
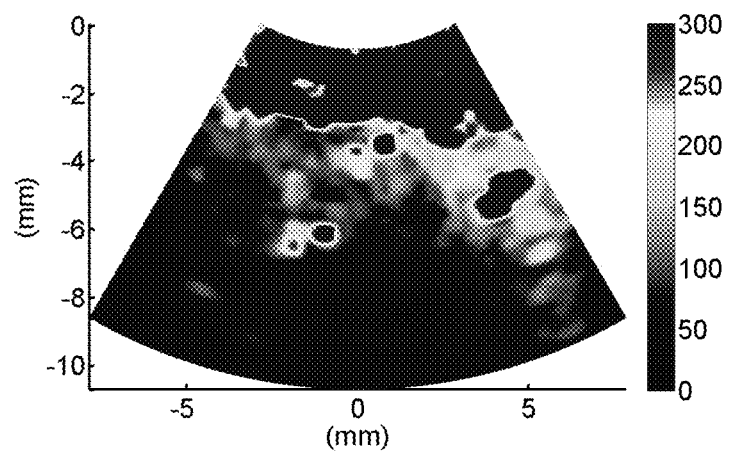
Figure 6D:
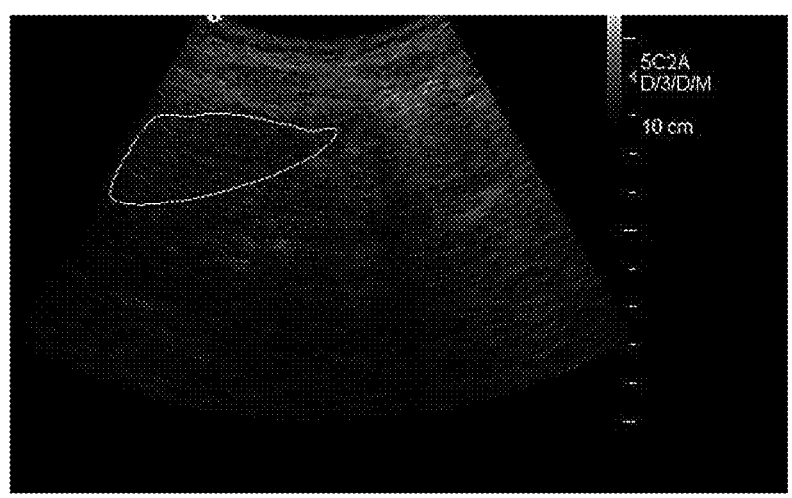
Figure 6E:
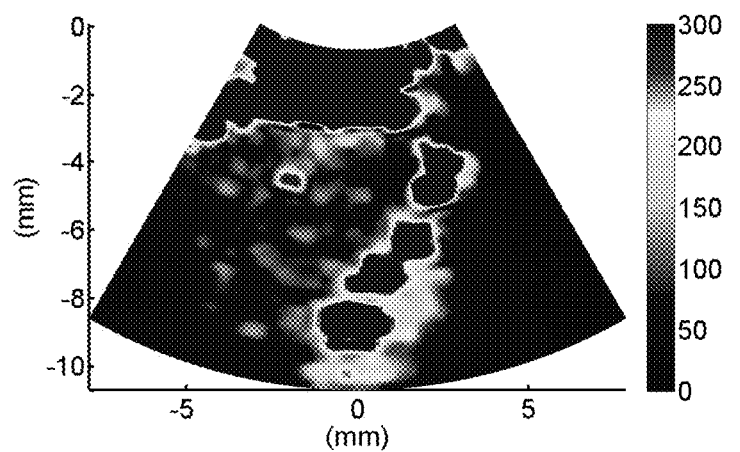
Figure 6E:
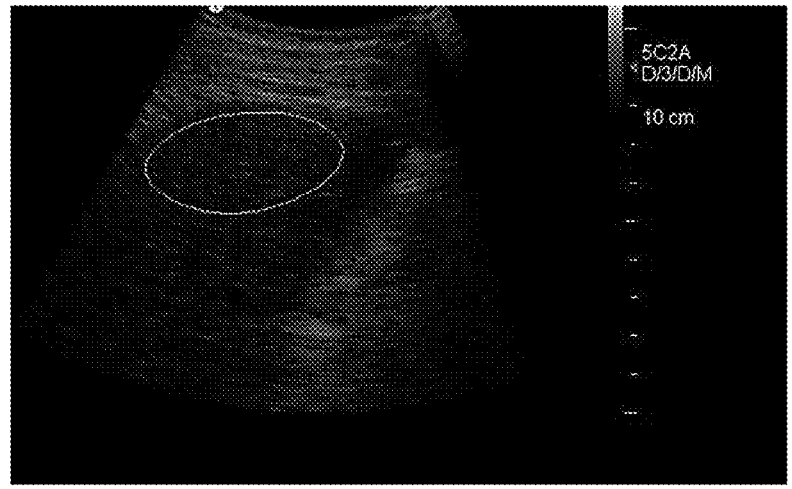
Figure 7A:
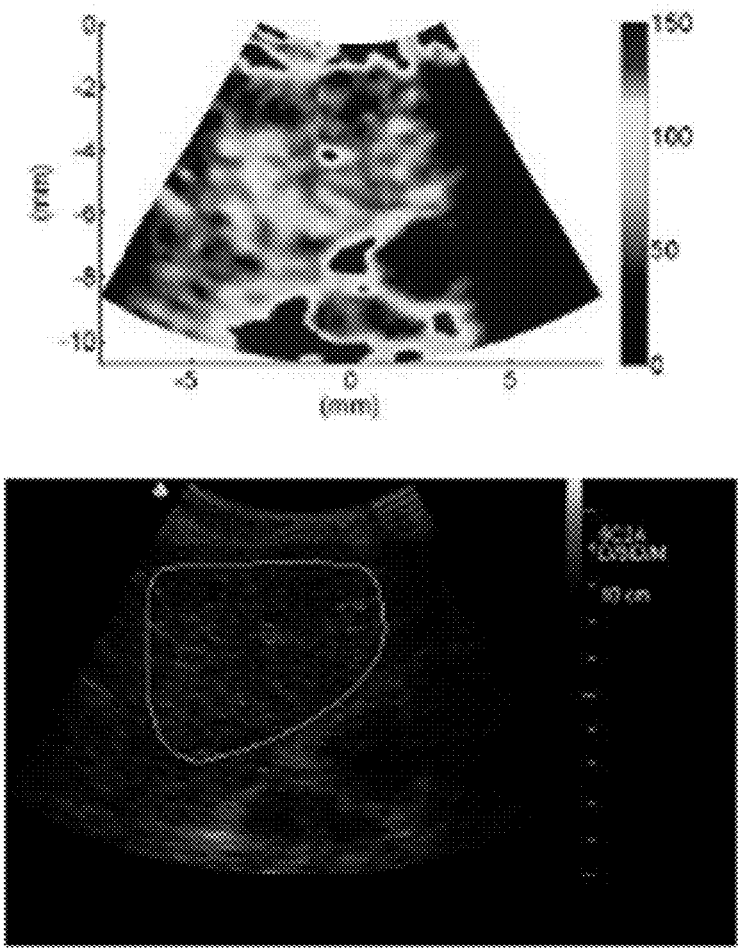
FIG. 7A to FIG. 7E show ultrasound scatterer mode images generated according to the formula 4 using third group setting listed on FIG. 4, and corresponding traditional grayscale ultrasound images.
Figure 7B:
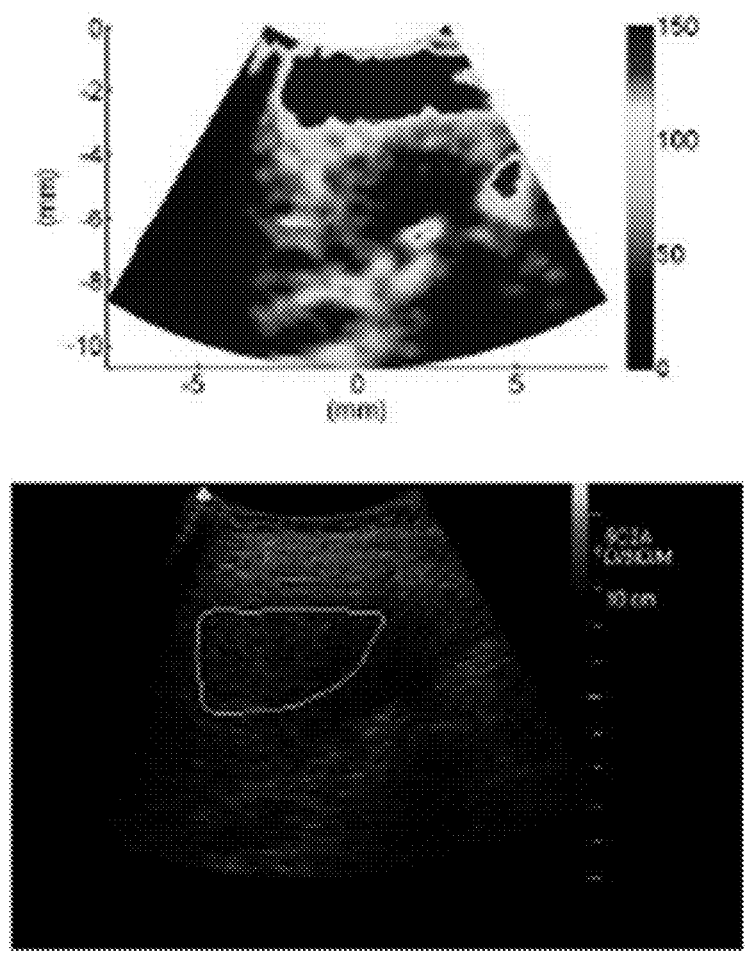
Figure 7C:
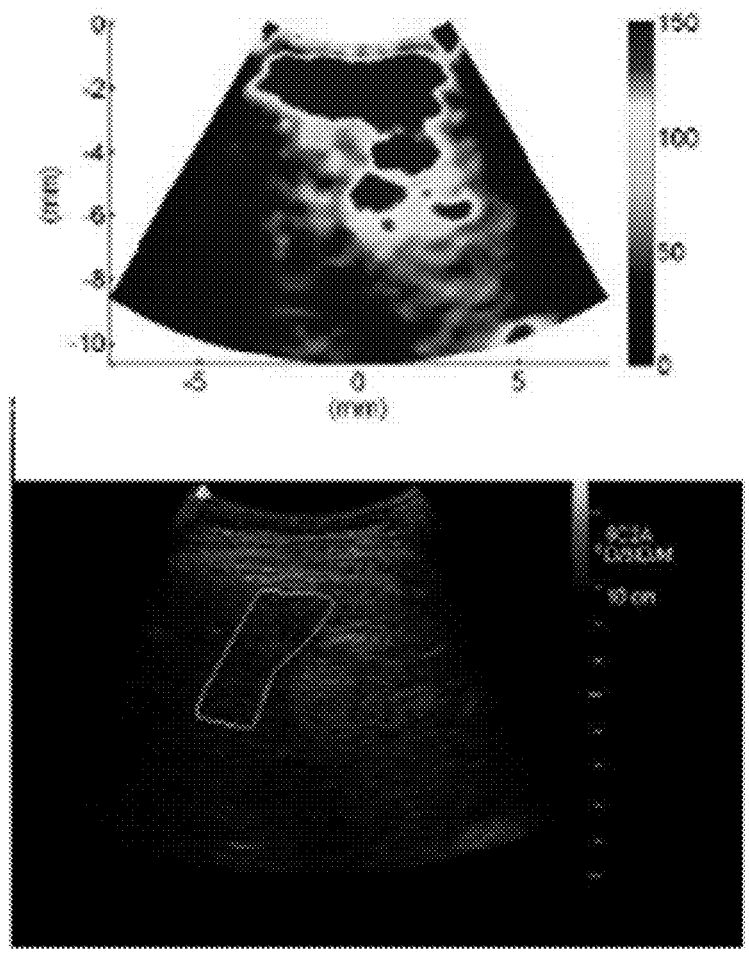
Figure 7D:
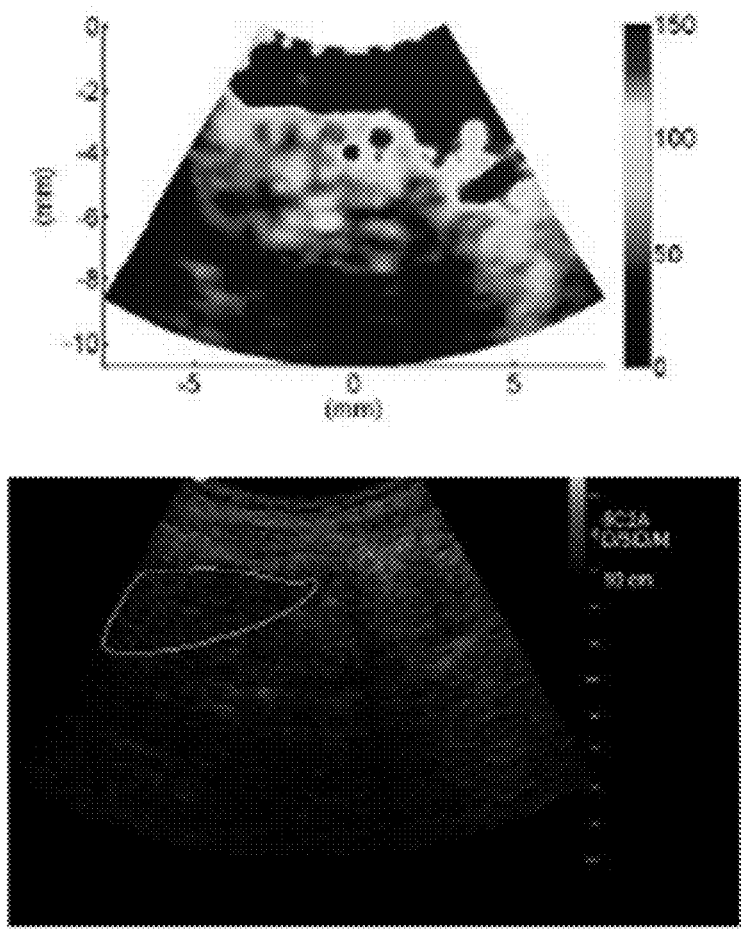
Figure 7E:
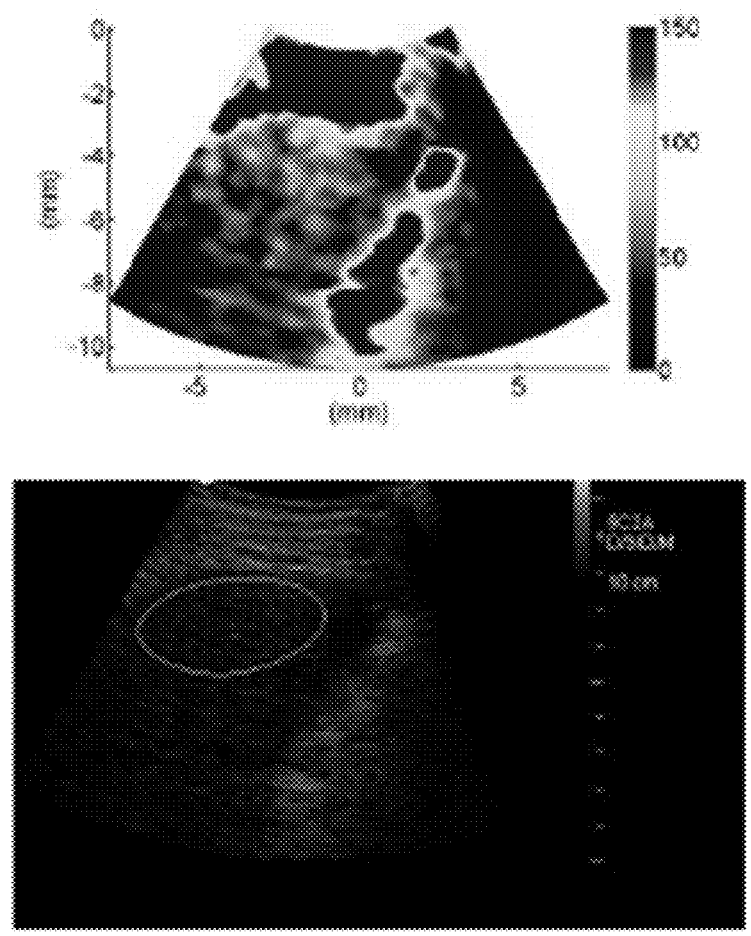

In addition, severity degrees of liver fibrosis can be effectively distinguished. It can be found that ultrasound scatterer mode image that displays ultrasound scatterer values by utilizing color scale. FIG. 5A, FIG. 6A, and FIG. 7A represent normal liver cases, while FIG. 5B to FIG. 5E, FIG. 6B to FIG. 6E, and FIG. 7B to FIG. 7E represent liver fibrosis from minor to severe corresponding to higher value to lower value of ultrasound scatterer value, respectively. The information may be useful in assisting the user's interpretation of the variation in tissue characteristics.

A flow chart 400 of a method for analyzing ultrasound echo signals based on statistics of scatterer distributions according to an embodiment of the present invention is shown in FIG. 13.

First, in step 410, a capturing device 210 captures an image of a tissue to obtain ultrasound image data 300, wherein the ultrasound image data 300 has a plurality of ultrasound echo signals, each having a signal image value.

Then, in step 420, choosing a first ultrasound echo signal as a center, an analyzing unit 220 calculates the signal image values of all ultrasound echo signals based on statistic method within a window block 330 in the ultrasound image data, to obtain a first ultrasound scatterer value.

In step 430, with a second ultrasound echo signal as a center, the analyzing unit 220 performs statistical analysis of the signal image values of all ultrasound echo signals within the window block 330 in the ultrasound image data, to obtain a second ultrasound scatterer value, wherein the second ultrasound echo signal is separated from the first ultrasound echo signal by at least one point distance.

For example, the window block 330 is moved laterally or longitudinally by a point distance 310 for lateral movement (for example, a six point distances) and a point distance 320 for longitudinal movement (for example, a thirty-six point distances).

In step 440, at intervals of the point distance, the analyzing unit 220 repeatedly calculates the signal image values of all ultrasound echo signals based on statistic methods within the window block 330 with the respective ultrasound echo signals as centers, to obtain a plurality of ultrasound scatterer values, until the first ultrasound scatterer value to an n-th ultrasound scatterer value being calculated include the signal image values of all the ultrasound echo signals in the ultrasound image data. When a point distance between the ultrasound echo signals is greater than one point distance, an interpolating function is used to obtain complete ultrasound scatterer values, wherein the ultrasound scatterer values are an MD of the signal image values, an ML of the signal image values, or any combination thereof.

Finally, in step 450, a display unit 230 outputs and displays an ultrasound scatterer mode image that displays the first ultrasound scatterer value to the n-th ultrasound scatterer value by utilizing color scale.

According to the system and the method for analyzing ultrasound echo signals based on statistics of scatterer distributions disclosed in the present invention, a user sets a window block 330 in an ultrasound image, then with an upper-left corner of the image as a starting position, calculates a ultrasound scatterer value according to a measure of dispersion (MD), a measure of location (ML) or any combination thereof. Then, when the window block 330 is moved by a fixed or non-fixed point distances, the ultrasound scatterer value is calculated. The steps are repeated until the window block 330 scans through the whole ultrasound image. Finally, an ultrasound scatterer mode image is formed that displays first ultrasound scatterer value to the n-th ultrasound scatterer value by utilizing color scale.

The system and the method for analyzing ultrasound echo signals based on statistics of scatterer distributions disclosed in the present invention are applicable to ultrasound image diagnosis for various organs. Compared with a traditional grayscale image, an ultrasound scatterer mode image generated by the present invention can provide more clinical information on tissue characterization. Particularly for distinguishing the blood vessels from normal tissue and identifying the walls of the blood vessels, and understanding position of the blood vessels can assist a physician in identifying the boundary of any organ (but not limited to liver) or the relative location of the organ with respect to its adjacent organs, which is convenient for providing clinical information.

The above embodiments are only provided to illustrate the principle and effects of the present invention, but not to limit. Thus, these embodiments can be modified and changed by persons skilled in the art without departing from the spirit. The scope of the present invention is subject to the attached claims.

REFERENCE NUMBERS 100-140, 400-450 steps
200 ultrasound image system
210 capturing device
220 analyzing unit
230 display unit
300 ultrasound image data
310 point distance for lateral movement
320 point distance for longitudinal movement
330 window block

The invention claimed is:

1. A method for analyzing ultrasound echo signals based on statistics of scatterer distributions, comprising steps of:
   obtaining an ultrasound image data, wherein the ultrasound image data has a plurality of ultrasound echo signals, each having a signal image value;
   choosing a first ultrasound echo signal as a center, calculating the signal image values of all ultrasound echo signals within a window block in the ultrasound image data, to obtain a first ultrasound scatterer value;
   choosing a second ultrasound echo signal as a center, calculating the signal image values of all ultrasound echo signals within the window block in the ultrasound image data, to obtain a second ultrasound scatterer value, wherein the second ultrasound echo signal is separated from the first ultrasound echo signal at least one point distance;
   at intervals of the point distance, repeatedly calculating the signal image values of all ultrasound echo signals within the window block with the respective ultrasound echo signals as centers, to obtain a plurality of ultrasound scatterer values, until the first ultrasound scatterer value to an n-th ultrasound scatterer value being obtained, wherein the ultrasound scatterer values are a measure of dispersion (MD) of the signal image values, a measure of location (ML) of the signal image values, or any combination thereof; and
   outputting an ultrasound scatterer mode image with the first ultrasound scatterer value of the first ultrasound echo signal to the n-th ultrasound scatterer value of the n-th ultrasound echo signal by utilizing color scale,
   wherein the ultrasound scatterer values are obtained by one of the following approaches:
   (a) dividing a first MD of the signal image values by a second MD of the signal image values, raising to a power constant, and multiplying by a weighting constant,
   (b) dividing a difference value between a first ML and a second ML of the signal image values by the MD of the signal image values, raising to a power constant, and multiplying by a weighting constant, and
   (c) dividing the MD of the signal image values by the ML of the signal image values, raising to a power constant, and multiplying by a weighting constant.

2. The method for analyzing ultrasound echo signals based on statistics of scatterer distributions of claim 1, wherein the ML is a mode value, a statistical percentile value, or a mean value.

3. The method for analyzing ultrasound echo signals based on statistics of scatterer distributions of claim 1, wherein the MD is a standard deviation value or a statistical range value.

* * * * *